United States Patent [19]

Stauffer

[11] Patent Number: 5,185,479
[45] Date of Patent: Feb. 9, 1993

[54] PROCESS FOR METHYL ALCOHOL

[76] Inventor: John E. Stauffer, 6 Pecksland Rd., Greenwich, Conn. 06831

[21] Appl. No.: 874,956

[22] Filed: Apr. 21, 1992

[51] Int. Cl.$^5$ .................. C07C 29/124; C07C 31/04; C07C 17/04
[52] U.S. Cl. .................. 568/893; 570/242; 570/243
[58] Field of Search .......................... 568/893

[56] References Cited

U.S. PATENT DOCUMENTS

| | | | |
|---|---|---|---|
| 2,447,410 | 8/1948 | Hampel | 570/220 |
| 2,484,702 | 10/1949 | Frey | 568/893 |
| 3,642,918 | 2/1972 | Bohl et al. | 570/224 |
| 4,523,040 | 6/1985 | Olah | 568/893 |
| 4,990,696 | 2/1991 | Stauffer | 568/893 |

FOREIGN PATENT DOCUMENTS 1468781  5/1969  Fed. Rep. of Germany ...... 568/893

Primary Examiner—Joseph E. Evans
Attorney, Agent, or Firm—Krass & Young

[57] ABSTRACT

An improved method of producing methyl alcohol (methanol) from methane is provided using two reaction steps operated in tandem. In the first reaction step two chemical reactions occur simultaneously: a) perchloroethylene ($CCl_2CCl_2$) is oxychlorinated with hydrogen chloride and oxygen to obtain hexachlorethane ($CCL_3CCL_3$) and water, and b) methyl chloride ($CH_3Cl$) is hydrolyzed with water to give methyl alcohol and hydrogen chloride. In the second reaction step methane is chlorinated with hexachlorethane to produce methyl chloride, hydrogen chloride and perchloroethylene. By recycling the methyl chloride, hydrogen chloride, and regenerated perchloroethylene produced in the second step to the first step the process can be operated in a balanced mode whereby the internal consumption of hydrogen chloride is equal to its formation.

6 Claims, 1 Drawing Sheet

PROCESS FOR METHYL ALCOHOL

FIELD OF THE INVENTION

The present invention relates to an improved method of producing methyl alcohol (methanol) from methane using two reaction steps operated in tandem. In the first reaction step two chemical reactions occur simultaneously: a) perchloroethylene ($CCl_1CCl_2$) is oxychlorinated with hydrogen chloride and oxygen to obtain hexachlorethane ($CCl_3CCl_3$) and water, and b) methyl chloride ($CH_3Cl$) is hydrolyzed with water to give methyl alcohol and hydrogen chloride. In the second reaction step methane is chlorinated with hexachlorethane to produce methyl chloride, hydrogen chloride and perchloroethylene. By recycling the methyl chloride, hydrogen chloride, and regenerated perchloroethylene produced in the second step to the first step the process can be operated in a balanced mode whereby the internal consumption of hydrogen chloride is equal to its formation. The process has the distinct advantage of providing high yields of product and offering significant cost savings over existing technology.

BACKGROUND OF THE INVENTION

A process for the manufacture of methyl alcohol is described in U.S. Pat. No. 4,990,696. The patent discloses a process involving three reaction steps operated in conjunction with each other. Beginning with the first step, perchloroethylene is oxychlorinated with hydrogen chloride and oxygen to obtain hexachloroethane. In the second step methane is chlorinated with hexachloroethane to produce methyl chloride, hydrogen chloride and regenerated perchloroethylene. The methyl chloride from the second step is isolated and hydrolyzed with water in the third step to give methyl alcohol and hydrogen chloride. The reactions are operated in a balanced mode by recycling perchloroethylene from the second step to the first step, and by recycling hydrogen chloride produced in each of the second and third steps to the first step.

A number of difficulties, however, are encountered with existing technology. Perhaps the greatest shortcoming is the unfavorable equilibrium in the hydrolysis reaction of methyl chloride with water to produce methyl alcohol. At ambient temperatures the reverse reaction, namely, the formation of methyl chloride from methyl alcohol and hydrogen chloride, is greatly favored. Elevated temperatures are required to shift the equilibrium, but even then only partial conversions are possible. Thus, an excess of water or steam is favored, and unreacted methyl chloride must be recycled to the hydrolysis reaction.

An additional problem identified with existing technology is the control of the temperature in the first step, namely, the oxychlorination reaction. This reaction is exothermic, and therefore heat must be removed to maintain the temperature at the desired setting. When a solid catalyst is used in this reaction, the possibility of hot spots developing on the catalyst particles ia potential problem.

Finally, the required investment in equipment must be considered. Since the existing technology involves the use of highly corrosive chemicals, especially aqueous hydrogen chloride streams, materials of construction can be a problem. Any reduction in the number of reaction steps and in the necessary unit operations, e.g., distillation, has the potential for substantial cost savings.

It is therefore an object of the present invention to provide a process that overcomes the disadvantages of existing technology for producing methyl alcohol.

A further object is to be able to produce high yields of product at minimum investment and operating costs.

These and other objects, features and advantages of the invention will be apparent from the accompanying drawing and the following description.

SUMMARY OF THE INVENTION

In one preferred embodiment of the invention, methyl chloride is hydrolyzed with water over a catalyst to give methyl alcohol and hydrogen chloride. Because of the limitations of equilibrium, this reaction would not proceed to any great extent save for the fact that the hydrogen chloride so formed is continually removed. The means of removing the hydrogen chloride is through the oxychlorination reaction which takes place in the same reactor. Hydrogen chloride reacts with oxygen in the presence of a catalyst to give chlorine and water. This reaction too, is limited by equilibrium conditions. The chlorine, however, is withdrawn by reacting it with perchloroethylene to form hexachloroethane. And water is withdrawn by reacting it with methyl chloride. Thus, by means of these cascade reactions, essentially all of the methyl chloride introduced to the reactor is hydrolyzed.

There is an additional benefit in conducting the hydrolysis reaction and oxychlorination reacting in intimate contact with each other. The hydrolysis reaction is endothermic, i.e., heat input is required to maintain the temperature of reaction. On the other hand, the oxychlorination reaction is exothermic, whereby heat is released. By combining these two reactions, the heat requirements can be better balanced since heat supplied by one reaction is absorbed by the other. This balancing allows for easier temperature control of the reactor and helps to avoid the development of potentially troublesome hot spots in the catalyst. The delayed release of half of the hydrogen chloride (that amount derived from the methyl chloride) further assists in the control of the reactor temperature. This design also provides for energy conservation.

Methyl chloride required for the hydrolysis reaction is produced by reacting methane with hexachloroethane in a thermal chlorination step. In this reaction, hexachloroethane decomposes to produce chlorine and perchloroethylene. The chlorine so formed reacts with the methane to give methyl chloride and hydrogen chloride. Again, an endothermic reaction (dissociation) is partly balanced with an exothermic reaction (chlorination) to provide improved temperature control.

The chemical reactions which occur in each of the reactors can be summarized by the following equations:

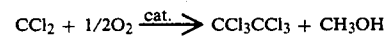

(2)

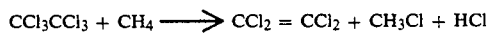

By combining equations 1 and 2 one obtains the following equation which represents the overall reaction:

(3) $CH_4 + \frac{1}{2}O_2 \rightarrow CH_3OH$

Thus, this process is shown to be a means of producing methyl alcohol from methane in high yields without the production of any coproducts.

BRIEF DESCRIPTION OF THE DRAWING

The invention will be better understood by reference to the preferred embodiments illustrated in the accompanying drawing.

DETAILED DESCRIPTION OF THE PROCESS

Figure 1:
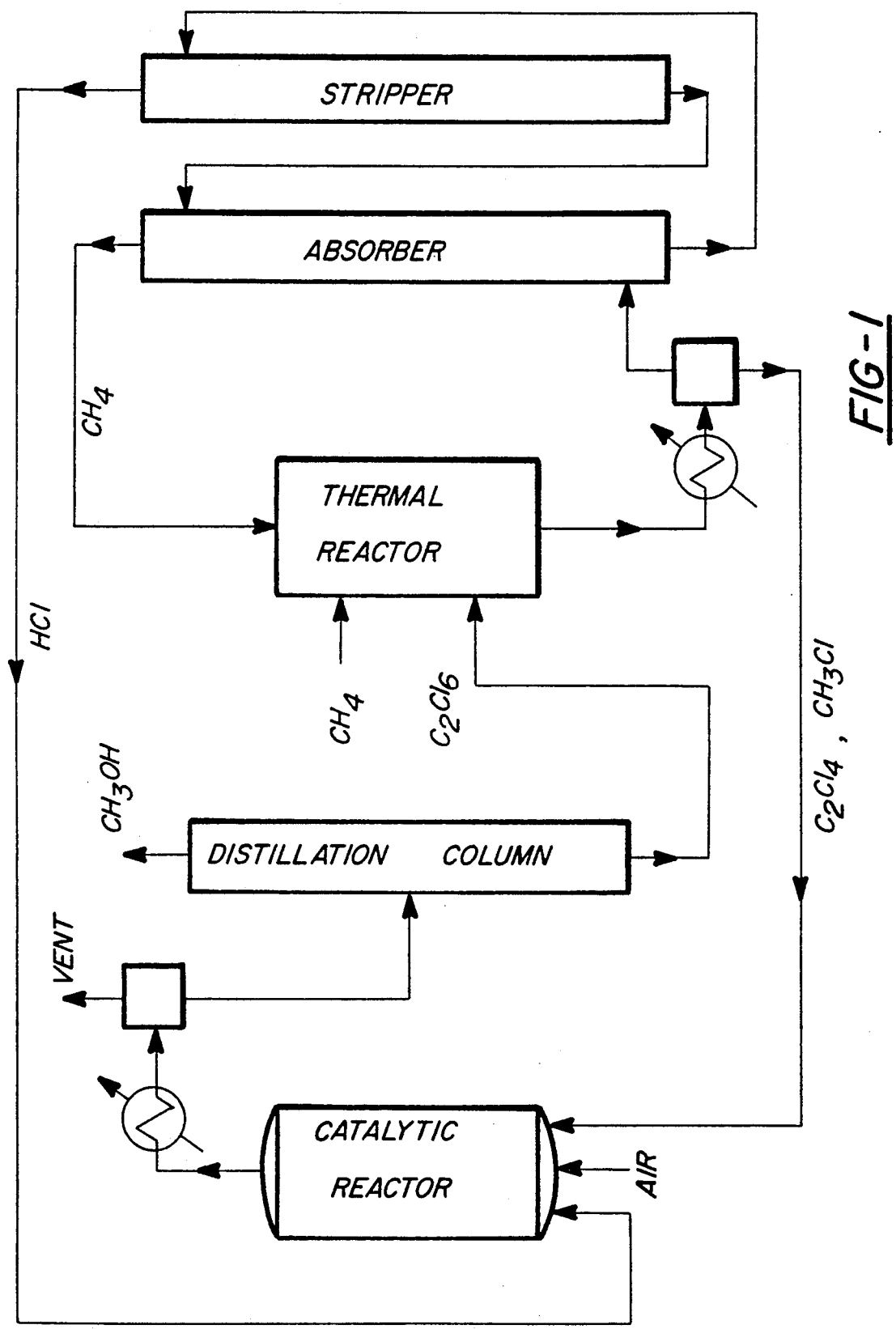
FIG. 1 is a flow sheet of the process showing the two reactors; key pieces of equipment including a distillation column, absorber and stripper columns; and recycle streams. By comparison with the existing technology described in the Background of the Invention, this flow sheet is relatively simplified and direct.

Oxychlorination is a reaction which has been investigated in some detail. The preferred catalyst for the reaction is a copper salt, e.g., copper chloride. This catalyst may be enhanced by the addition of other metal salts including iron, potassium and lead. Numerous other salts have been mentioned in the literature, e.g., rare earths, as having a beneficial effect on the reaction.

The oxychlorination catalyst may be deposited on an inert support for use in a shell and tube reactor or fluidized bed reactor. Alternatively, the catalyst may be in the form of a molten salt for use in a reactor designed for this application. A fairly wide temperature range has been used for the reaction, but generally temperatures between about 200° C. and about 375° C. are preferred.

The hydrolysis of methyl chloride to methyl alcohol has also been widely studied as the reverse reaction. Since reaction conditions are identical for the forward and reverse reaction, the reported data are relevant to the present invention. The hydrolysis reaction is promoted by a catalyst such as copper chloride, zinc chloride, nd bismuth chloride. Other catalysts such as alumina gel have also been used. However, high-area aluminas, which have acidic sites on the surface, have been shown to promote the dehydration of methanol to form dimethyl ether. The reaction may be carried out in the vapor phase in the temperature range of 280° C. to 350° C. Methyl chloride has also been produced from methyl alcohol in a liquid phase reaction by refluxing the alcohol at 150° C with hydrochloric acid in the presence of zinc chloride.

From these data, one can readily appreciate the fact that the two reactions, oxychlorination and hydrolysis, can be combined into one reaction step, thereby producing the desired synergism. For the combined reaction the preferred temperature would be in the range of 200° C. to 375° C. The favored catalyst would be copper chloride enhanced by other metal chlorides selected from the group, potassium chloride, iron chloride, zinc chloride, lead chloride, and bismuth chloride. This list is not meant to be restrictive, there being many other compounds that have been tried successfully in these applications.

The chlorination of methane is typically conducted in the vapor phase at elevated temperatures preferably in the range from about 400° C. to about 700° C. Pressures in the neighborhood of one atmosphere absolute are used in this thermal reactor. The probable mechanism by which methane is chlorinated is a series of free-radical reactions. Normally higher chlorinated methane including methylene chloride, chloroform, and carbon tetrachloride would be produced along with methyl chloride. In the present invention, however, the formation of these higher chlorinated compounds is suppressed by using an excess of methane and by approximating plug flow conditions in the chlorination reactor. The latter feature can be achieved by incorporating a static or motionless mixer in the reactor. Careful temperature control is also important. This requirement was discussed earlier.

There have been reports in the literature about the catalytic monohalogenation of methane using either supported acid or platinum metal catalysts. Selectivity is claimed to be in the range of 85-99%. This process, however, is not known to have been practiced on a large scale.

The recycle and feed streams are shown on the accompanying figure. Certain precautions are advisable for successful operation. For example, the feed streams to the chlorination reactor should be dried to avoid potential corrosion problems. Generally air is supplied to the catalyst reactor as a source of oxygen. Alternatively mixtures of air and oxygen may be used, the rationale being to increase the capacity of the reactor or to minimize vent effluents. Generally, the catalyst reactor is operated at close to one atmosphere absolute.

Some dimethyl ether may be formed in the catalytic reactor, although the quantity would be significantly reduced compared with existing technology. This byproduct may be recycled to the reactor for conversion to methyl alcohol or treated externally to the process. Methods of converting alcohol to ether and the reverse reaction are well known in the art.

Methyl alcohol produced by the methods of the present invention is a valuable item of commerce. Substantial quantities of methyl alcohol are converted to formaldehyde which is a component of several plastics. Methyl alcohol shows promise as a general motor fuel. Widespread use of methyl alcohol in internal combustion engines would reduce air pollution caused by the emission of exhaust fumes. Such improvements can be gained without significantly impairing engine performance.

The embodiments of the present invention in which exclusive property or privilege is claimed are defined as follows.

I claim:

1. A process for the production of methyl alcohol from methane comprising the following steps operated in tandem:

first, reacting methyl chloride, hydrogen chloride, perchloroethylene and oxygen in the presence of a catalyst to give reaction products comprising methyl alcohol and hexachloroethane; separating the methyl alcohol product from the hexachloroethane; and second, reacting the isolated hexachloroethane from the first step with methane to produce methyl chloride, hydrogen chloride and perchloroethylene, which are separated from any unreacted methane before being recycled to the first step.

2. A process according to claim 1 in which the source of oxygen for the first step is air.

3. A process according to claim 1 in which the catalyst used in the first step comprises copper chloride.

4. A process according to claim 3 where the catalyst comprises an admixture of copper chloride with a salt selected from the group consisting of potassium chloride, ferric chloride, lead chloride, zinc chloride, and bismuth chloride.

5. A process according to claim 1 in which the catalytic reaction is carried out at a temperature in the range from about 200° C. to about 375° C.

6. A process according to claim 1 in which the reaction in the second step is carried out in the vapor phase at a temperature in the range from about 400° C. to about 700° C.

* * * * *